United States Patent
Mizutani et al.

(10) Patent No.: US 10,788,448 B2
(45) Date of Patent: Sep. 29, 2020

(54) GAS SENSOR

(71) Applicant: DENSO CORPORATION, Kariya, Aichi-pref. (JP)

(72) Inventors: Keigo Mizutani, Nisshin (JP); Keisuke Mizutani, Nisshin (JP); Mitsunobu Nakato, Kariya (JP); Takashi Araki, Kariya (JP)

(73) Assignee: DENSO CORPORATION, Kariya (JP)

( * ) Notice: Subject to any disclaimer, the term of this patent is extended or adjusted under 35 U.S.C. 154(b) by 267 days.

(21) Appl. No.: 16/070,601

(22) PCT Filed: Nov. 3, 2016

(86) PCT No.: PCT/JP2016/082722
§ 371 (c)(1),
(2) Date: Jul. 17, 2018

(87) PCT Pub. No.: WO2017/126190
PCT Pub. Date: Jul. 27, 2017

(65) Prior Publication Data
US 2019/0025248 A1 Jan. 24, 2019

(30) Foreign Application Priority Data
Jan. 19, 2016 (JP) ................................. 2016-008173

(51) Int. Cl.
*G01N 27/417* (2006.01)
*G01N 27/407* (2006.01)
(Continued)

(52) U.S. Cl.
CPC ......... *G01N 27/419* (2013.01); *G01N 27/409* (2013.01); *G01N 27/4072* (2013.01); *G01N 27/41* (2013.01); *G01N 33/0036* (2013.01)

(58) Field of Classification Search
CPC ....... G01N 27/404–407; G01N 27/409; G01N 27/419; G01N 27/41; G01N 27/4072; G01N 27/4067; G01N 27/4074; G01N 27/417; G01N 27/4045; F02D 41/123; F02D 41/1454; F02D 41/146
See application file for complete search history.

(56) References Cited

U.S. PATENT DOCUMENTS

| | | |
|---|---|---|
| 6,319,377 B1 | 11/2001 | Hasei et al. |
| 2002/0104758 A1 | 8/2002 | Mizutani et al. |
| 2016/0320334 A1 | 11/2016 | Nakatou et al. |

FOREIGN PATENT DOCUMENTS

JP 2001-21535 1/2001

*Primary Examiner* — Gurpreet Kaur
(74) *Attorney, Agent, or Firm* — Nixon & Vanderhye P.C.

(57) ABSTRACT

A gas sensor which can improve an accuracy in detecting a specific gas component by properly correcting for the influence of residual oxygen is provided. The gas sensor includes a solid electrolyte plate, a measured gas chamber into which a measured gas flows, a pump cell which adjusts an oxygen concentration of the measured gas using a pump electrode, a monitor cell which detects a residual oxygen concentration of the measured gas using a monitor electrode, and a sensor cell which detects a specific gas component concentration of the measured gas using a sensor electrode. The maximum thickness of the sensor electrode is greater than the maximum thickness of the monitor electrode, and the difference between the maximum thickness of the sensor electrode and the maximum thickness of the monitor electrode is between 4 μm and 30 μm, inclusive.

15 Claims, 11 Drawing Sheets

(51) Int. Cl.
*G01N 27/409* (2006.01)
*G01N 33/00* (2006.01)
*G01N 27/419* (2006.01)
*G01N 27/41* (2006.01)

GAS SENSOR

CROSS REFERENCE TO RELATED APPLICATIONS

This application is the U.S. national phase of International Application No. PCT/JP2016/082722 filed Nov. 3, 2016 which designated the U.S. and claims priority to Japanese Patent Application No. 2016-8173 filed Jan. 19, 2016, the entire contents of each of which are hereby incorporated by reference.

TECHNICAL FIELD

The present disclosure relates to a gas sensor which measures the concentration of a specific gas component in a measured gas.

BACKGROUND ART

A gas sensor which measures the concentration of a specific gas component such as $NO_x$ in a measured gas detects the concentration of the specific gas component in the measured gas using a sensor electrode capable of decomposing the specific gas component after adjusting the oxygen concentration of the measured gas to be equal to or less than a predetermined concentration. Furthermore, upon this detection of the concentration of the specific gas component, the concentration of residual oxygen in the measured gas having the adjusted oxygen concentration is detected using a monitor electrode different from the sensor electrode, and an influence that the concentration of the residual oxygen has on the detection of the concentration of the specific gas component is corrected.

For example, in the gas sensor element disclosed in Patent Literature (PTL) 1, an oxygen pump cell, an oxygen monitor cell, and a sensor cell are formed using solid electrolyte sheets and a pair of electrodes. The oxygen monitor cell detects residual oxygen in a measured gas having an oxygen concentration adjusted by the oxygen pump cell, and the sensor cell detects the residual oxygen and a specific gas component in the measured gas having the oxygen concentration adjusted by the oxygen pump cell. Subsequently, the output of the oxygen monitor cell is subtracted from the output of the sensor cell, and thus the concentration of the specific gas component in the measured gas is detected. In this gas sensor element, an electrode (referred to as a monitor electrode) that is disposed in the oxygen monitor cell and is exposed to the measured gas and an electrode (referred to as a sensor electrode) that is included in the sensor cell and is exposed to the measured gas are disposed in substantially symmetrical positions with respect to a direction in which the gas flows. Thus, the measured gas contacts the monitor electrode and the sensor electrode equally so that the concentration of the residual oxygen detected by the oxygen monitor cell and the concentration of the residual oxygen detected by the sensor cell become substantially equal.

CITATION LIST

Patent Literature

[PTL 1] JP 3973900 B

SUMMARY OF THE INVENTION

In conventional gas sensors including the one disclosed in PTL 1, there is no devise found in the relationship between the thickness of a monitor electrode and the thickness of a sensor electrode. That is, it was found that the thickness of the monitor electrode and the thickness of the sensor electrode need to be properly determined to improve the accuracy in detecting the concentration of a specific gas component.

The present disclosure is a result of efforts to provide a gas sensor which can improve the accuracy in detecting a specific gas component by properly correcting for the influence of residual oxygen.

One aspect of the present disclosure is a gas sensor including:

one or more solid electrolyte plate having oxygen ion conductivity;

a measured gas chamber formed adjacent to the solid electrolyte plate;

a pump electrode which is provided on a surface of the solid electrolyte plate and is exposed to a measured gas in the measured gas chamber;

a monitor electrode and a sensor electrode which are provided adjacent to each other on the surface of the solid electrolyte plate, in positions downstream of the pump electrode in a flow direction of the measured gas, and are exposed to the measured gas in the measured gas chamber;

one or more reference electrode which is provided on a surface of the solid electrolyte plate and is exposed to a reference gas;

a heater which is disposed facing the solid electrolyte plate and heats the solid electrolyte plate;

a pump cell which adjusts an oxygen concentration of the measured gas in the measured gas chamber when a voltage is applied between the pump electrode and the reference electrode through a portion of the solid electrolyte plate;

a monitor cell which detects an electric current flowing between the monitor electrode and the reference electrode through a portion of the solid electrolyte plate, and detects residual oxygen in the measured gas having the oxygen concentration adjusted by the pump electrode; and a sensor cell which detects an electric current flowing between the sensor electrode and the reference electrode through a portion of the solid electrolyte plate, and detects the residual oxygen and a specific gas component in the measured gas having the oxygen concentration adjusted by the pump electrode, wherein a maximum thickness of the sensor electrode is greater than a maximum thickness of the monitor electrode, and a difference between the maximum thickness of the sensor electrode and the maximum thickness of the monitor electrode is between 4 µm and 30 µm, inclusive.

Advantageous Effects of the Invention

In the above-mentioned gas sensor, the relationship between the maximum thickness of the monitor electrode used for detecting the residual oxygen concentration of the measured gas and the maximum thickness of the sensor electrode used for detecting the specific gas component concentration is defined. Specifically, the maximum thickness of the sensor electrode is greater than the maximum thickness of the monitor electrode. The measured gas having the oxygen concentration adjusted by the pump electrode contacts the monitor electrode and the sensor electrode. Subsequently, the monitor electrode decomposes the residual oxygen in the measured gas, whereas the sensor electrode decomposes the residual oxygen and the specific gas component in the measured gas.

Although it is sufficient that the monitor electrode contains a component that decomposes oxygen, the sensor electrode needs to contain, in addition to a component that decomposes oxygen, a component that decomposes the specific gas component. Thus, the component that is included in the sensor electrode and decomposes oxygen is relatively less in amount than the component that is included in the monitor electrode and decomposes oxygen. As a result, the oxygen decomposition ability of the sensor electrode per unit volume is less than the oxygen decomposition ability of the monitor electrode per unit volume. Then, in order to balance between the oxygen decomposition ability of the monitor electrode and the oxygen decomposition ability of the sensor electrode, setting the maximum thickness of the sensor electrode greater than the maximum thickness of the monitor electrode is effective. Thus, as a result of balancing between the oxygen decomposition ability of the monitor electrode and the oxygen decomposition ability of the sensor electrode, the accuracy in detecting a specific gas component by the gas sensor can be improved.

Note that in the gas sensor, the influence that the residual oxygen has on the detection of the specific gas component can be corrected by subtracting the output of the monitor cell from the output of the sensor cell.

Further, a difference between the maximum thickness of the sensor electrode and the maximum thickness of the monitor electrode is set between 4 µm and 30 µm, inclusive. If the maximum thickness of the sensor electrode is excessively greater than the maximum thickness of the monitor electrode, the sensitivity of the sensor electrode to the specific gas component would become high, but the sensitivity of the sensor electrode to the residual oxygen may become excessively greater than the sensitivity of the monitor electrode to the residual oxygen. Therefore, by setting the difference between the maximum thickness of the sensor electrode and the maximum thickness of the monitor electrode equal to or less than 30 µm, the difference between the sensitivity of the sensor electrode to the residual oxygen and the sensitivity of the monitor electrode to the residual oxygen can be prevented from becoming large. Thus, as a result of properly correcting for the influence the residual oxygen has on the detection of the specific gas component, the accuracy in detecting the specific gas component by the gas sensor can be improved.

However, in order to balance between the oxygen decomposition ability of the monitor electrode and the oxygen decomposition ability of the sensor electrode, the maximum thickness of the sensor electrode needs to be at least 4 µm greater than the maximum thickness of the monitor electrode.

Thus, with the above-mentioned gas sensor, the accuracy in detecting the specific gas component can be improved by properly correcting for the influence of the residual oxygen.

BRIEF DESCRIPTION OF THE DRAWINGS

The objects, features, advantages, etc., of the present disclosure will become more apparent from the following detailed description taken in conjunction with the accompanying drawings. The drawings of the present disclosure are indicated below.

DESCRIPTION OF THE EMBODIMENTS

A preferred embodiment of the above-described gas sensor will be described with reference to the drawings.

Figure 1:
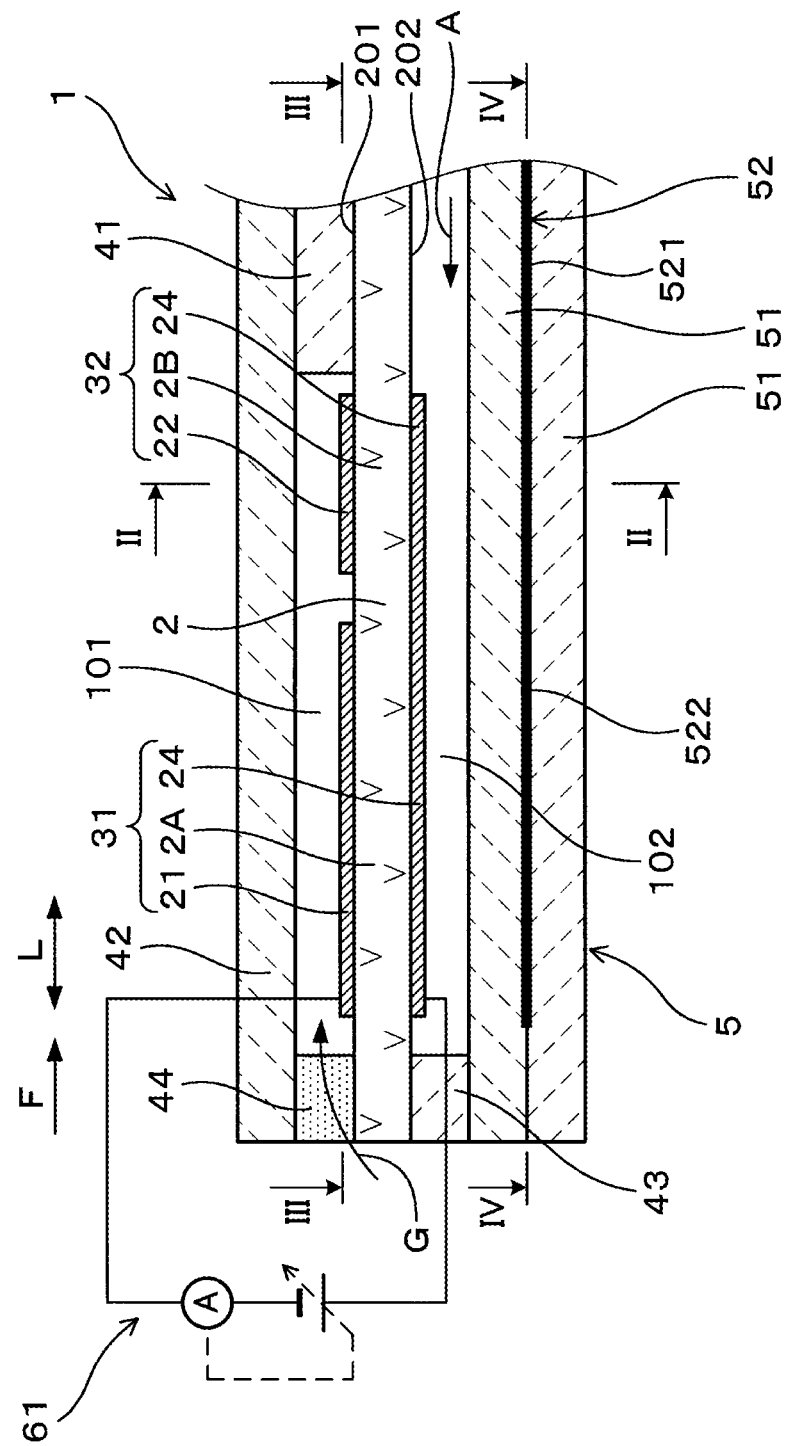
FIG. 1 illustrates a cross sectional view of a gas sensor according to an embodiment.
Figure 2:
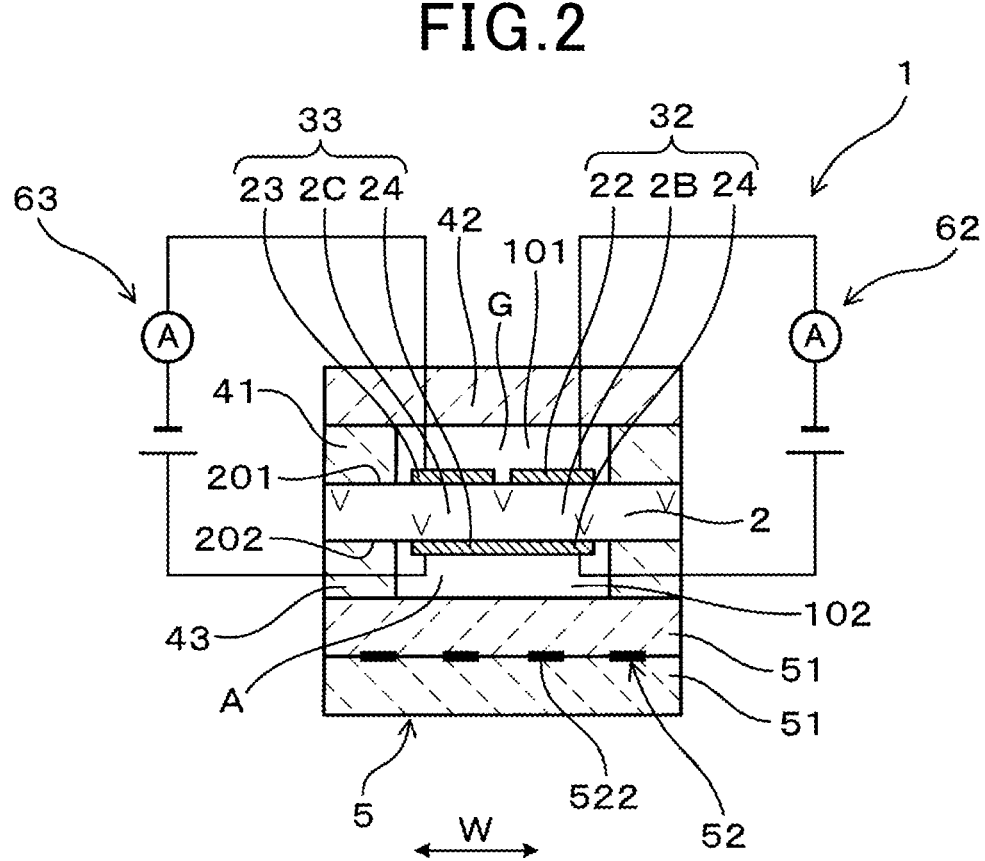
FIG. 2 illustrates a cross sectional view of the gas sensor according to the embodiment, taken in a direction of arrows II-II in FIG. 1.
Figure 3:
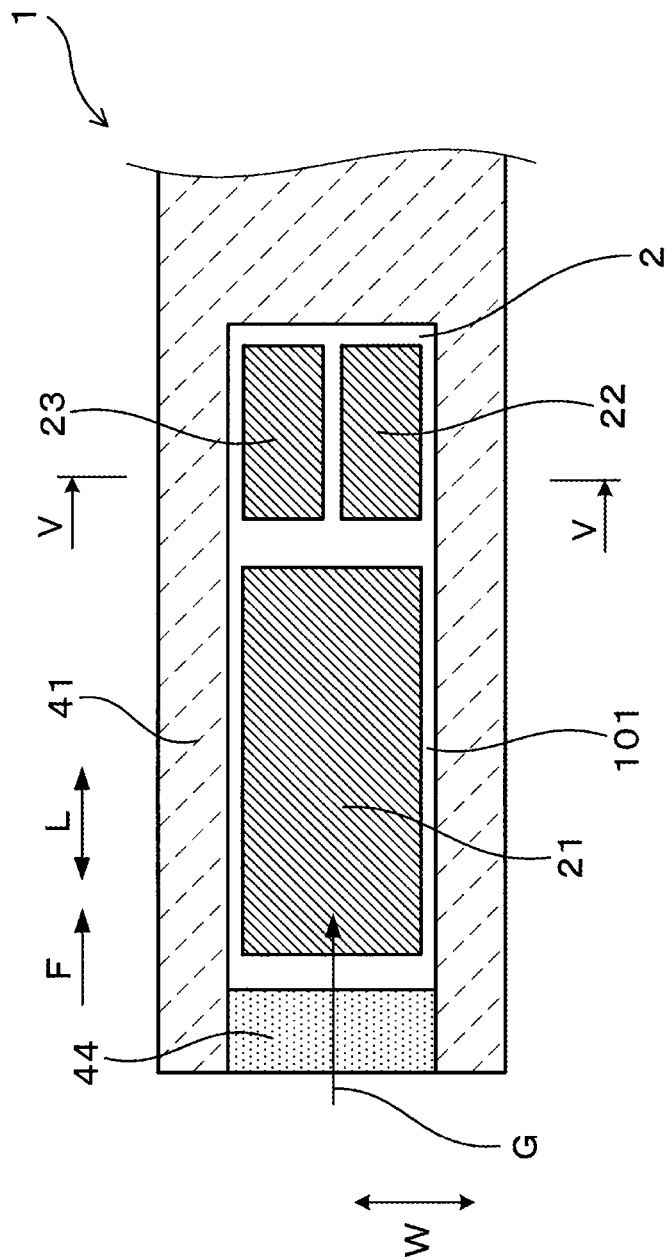
FIG. 3 illustrates a cross sectional view of the gas sensor according to the embodiment, taken in a direction of arrows III-III in FIG. 1.

As shown in FIGS. 1 to 3, a gas sensor 1 includes a solid electrolyte plate 2, a measured gas chamber 101, a pump electrode 21, a monitor electrode 22, a sensor electrode 23, a reference electrode 24, a heater 5, a pump cell 31, a monitor cell 32, and a sensor cell 33.

The solid electrolyte plate 2 has oxygen ion conductivity. The measured gas chamber 101 is formed adjacent to the solid electrolyte plate 2. The pump electrode 21 is provided on a first surface 201, which is one surface of the solid electrolyte plate 2 and is exposed to a measured gas G in the measured gas chamber 101. The monitor electrode 22 and the sensor electrode 23 are provided adjacent to each other on the first surface 201 of the solid electrolyte plate 2, in positions downstream of the pump electrode 21 in a flow F of the measured gas G and are exposed to the measured gas G in the measured gas chamber 101.

The reference electrode 24 is provided on a second surface 202, which is the other surface of the solid electrolyte plate 2, and is exposed to a reference gas A. The heater 5 is disposed facing the solid electrolyte plate 2 and heats the solid electrolyte plate 2. The pump cell 31 adjusts the oxygen concentration of the measured gas G in the measured gas chamber 101 when a voltage is applied between the pump electrode 21 and the reference electrode 24 through a first portion 2A of the solid electrolyte plate 2. The monitor cell 32 detects an electric current flowing between the monitor electrode 22 and the reference electrode 24 through a second portion 2B of the solid electrolyte plate 2 and detects residual oxygen in the measured gas G having the oxygen concentration adjusted by the pump electrode 21. The sensor cell 33 detects an electric current flowing between the sensor electrode 23 and the reference electrode 24 through a third portion 2C of the solid electrolyte plate 2 and detects the residual oxygen and a specific gas component in the measured gas G having the oxygen concentration adjusted by the pump electrode 21.

Figure 5:
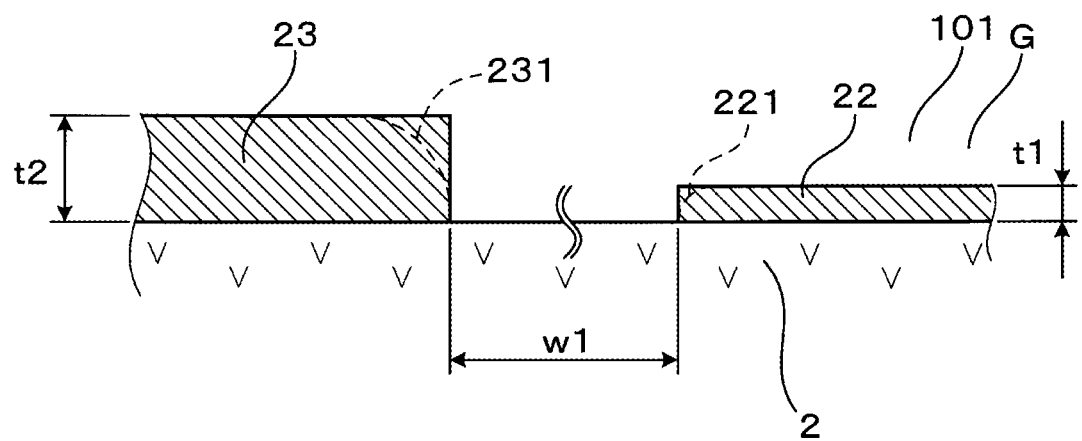
FIG. 5 illustrates the maximum thickness of a monitor electrode and the maximum thickness of a sensor electrode according to the embodiment.

As shown in FIG. 5, a maximum thickness t2 of the sensor electrode 23 is greater than a maximum thickness t1 of the monitor electrode 22, and the difference between the maximum thickness t2 of the sensor electrode 23 and the maximum thickness t1 of the monitor electrode 22 is between 4 µm to 30 µm, inclusive.

Note that the illustration of the monitor electrode 22, the sensor electrode 23, etc., in FIGS. 1, 2, etc., is conceptual and does not indicate the actual thicknesses, etc., of the monitor electrode 22, the sensor electrode 23, etc.

Hereinafter, the gas sensor 1 according to the present embodiment will be described in further detail.

Figure 6:
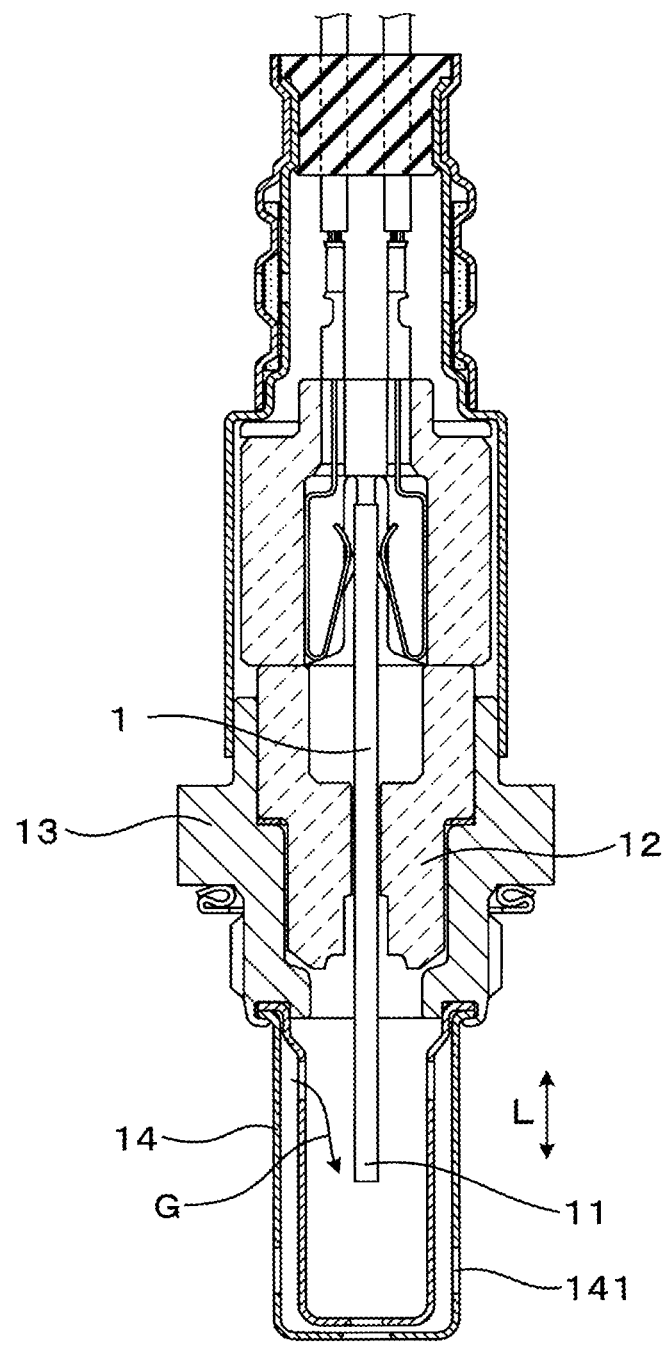
FIG. 6 illustrates a state of the gas sensor according to the embodiment when mounted to an internal combustion engine.

The gas sensor 1 is disposed and used in an exhaust passage of an internal combustion engine in a vehicle and detects, assuming that an exhaust gas flowing through the exhaust passage is the measured gas G, the concentration of $NO_x$ (nitrogen oxide) which is regarded as the specific gas component contained in the exhaust gas. As shown in FIG. 6, the gas sensor 1 is formed in an elongated shape and included in a sensor element. A portion on a base end of the gas sensor 1 in a longitudinal direction L is held by an insulator 12, and the insulator 12 is held by a housing 13 mounted on the internal combustion engine. Furthermore, a sensing unit 11 into which the measured gas G flows is provided on a portion on a leading end of the gas sensor 1 in the longitudinal direction L, and the sensing unit 11 is covered by a protective cover 14 having a through-hole 141. The measured gas chamber 101, the pump electrode 21, the monitor electrode 22, the sensor electrode 23, the reference electrode 24, the heater 5, the pump cell 31, the monitor cell 32, the sensor cell 33, and the like are disposed in the sensing unit 11.

In the present embodiment, the leading end of the gas sensor 1 in the longitudinal direction L is upstream side in the flow F of the measured gas G in the measured gas chamber 101, and the base end of the gas sensor 1 in the longitudinal direction L is downstream side in the flow F of the measured gas G in the measured gas chamber 101.

As shown in FIGS. 1 and 2, the gas sensor 1 includes only one solid electrolyte plate 2, which is made of yttria-stabilized zirconia. A second insulating plate 42 is laminated above the first surface 201 of the solid electrolyte plate 2 via a first insulating plate 41 having a cutout shape for forming the measured gas chamber 101. Each of the first insulating plate 41 and the second insulating plate 42 is made of an insulating material such as alumina. The first insulating plate 41 is provided on each of the portion on the base end in the longitudinal direction L and portions at both ends in a width direction W at the first surface 201 of the solid electrolyte plate 2. An opening is formed at a portion on the leading end of the first insulating plate 41 in the longitudinal direction L, and a diffusion resistor 44 made of porous bodies is disposed in this opening. The measured gas chamber 101 is formed having four sides enclosed by the diffusion resistor 44 and the first insulating plate 41, between the first surface 201 of the solid electrolyte plate 2 and the second insulating plate 42. The measured gas G flows into the measured gas chamber 101 through the diffusion resistor 44.

As shown in FIGS. 1 and 3, the pump electrode 21, the monitor electrode 22, the sensor electrode 23, and the reference electrode 24 are provided on the same solid electrolyte plate 2. The pump electrode 21 is disposed in the measured gas chamber 101 in a position that is upstream side in the flow F of the measured gas G and is disposed closer to the diffusion resistor 44 than the monitor electrode 22 and the sensor electrode 23 are. The monitor electrode 22 and the sensor electrode 23 are formed having substantially equal sizes and are disposed in substantially the same positions relative to the pump electrode 21. Furthermore, the conditions for disposing the monitor electrode 22 and the sensor electrode 23 are made substantially the same relative to the flow F of the measured gas G that has passed through the position in which the pump electrode 21 is disposed in the measured gas chamber 101.

Furthermore, as shown in FIG. 5, a distance w1 between the monitor electrode 22 and the sensor electrode 23 disposed on the solid electrolyte plate 2 is preferably set to equal to or less than 1.0 mm. When the distance w1 between the monitor electrode 22 and the sensor electrode 23 is short, the flow rate, components, etc., of the measured gas G which contacts each of these electrodes 22 and 23 are easily made substantially the same.

One reference electrode 24 is provided in a position facing all of the pump electrode 21, the monitor electrode 22, and the sensor electrode 23. In addition to this, three reference electrodes 24 may be separately provided in positions that are respectively facing the pump electrode 21, the monitor electrode 22, and the sensor electrode 23.

Each of the pump electrode 21 and the monitor electrode 22 is composed by using a cermet material which can decompose oxygen, but does not decompose the specific gas component, and contains a metal component such as a Pt-Au alloy and a zirconia component. The sensor electrode 23 is composed by using a cermet material which can decompose oxygen and the specific gas component and contains a metal component such as a Pt-Rh alloy and a zirconia component. The reference electrode 24 is composed by using a cermet material which can decompose oxygen and contains a metal component such as Pt and a zirconia component.

Figure 4:
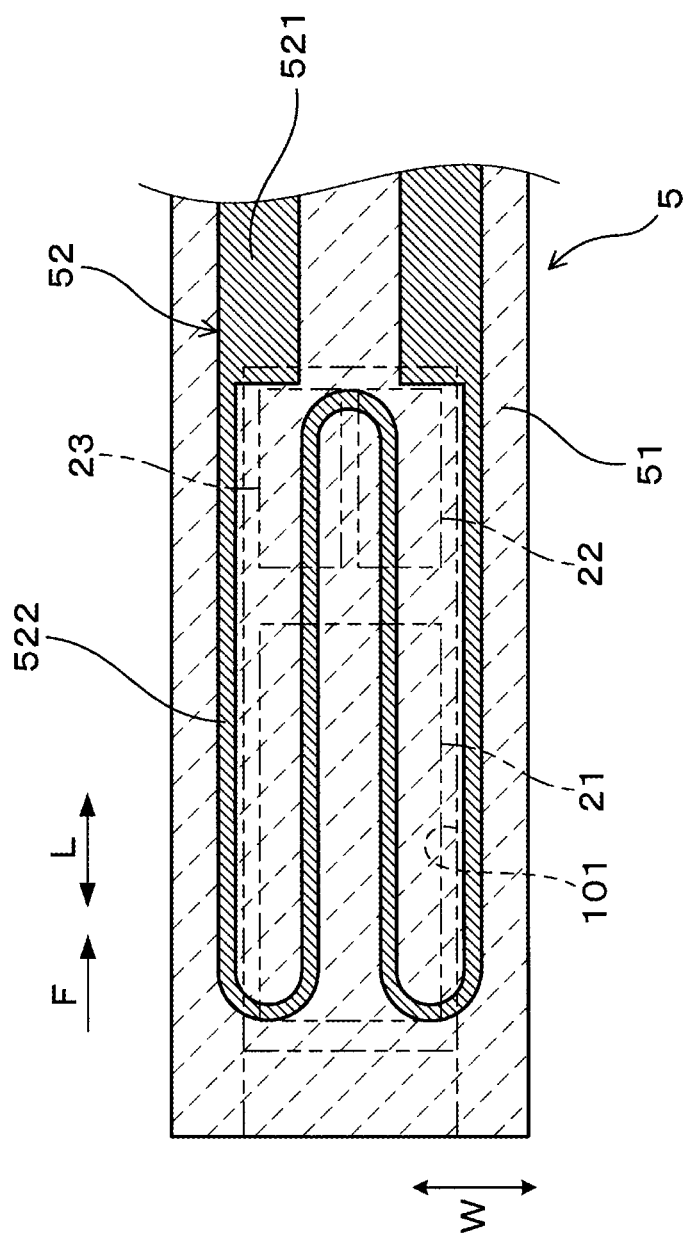
FIG. 4 illustrates a cross sectional view of the gas sensor according to the embodiment, taken in a direction of arrows IV-IV in FIG. 1.

As shown in FIGS. 1, 2, and 4, the heater 5 includes two ceramic substrates 51 made of alumina, and a conductor layer 52 embedded between the two ceramic substrates 51. The heater 5 is laminated above the second surface 202 of the solid electrolyte plate 2 via a third insulating plate 43 for forming the reference gas chamber 102 into which air as the reference gas A is introduced. The third insulating plate 43 is made of an insulating material such as alumina.

The third insulating plate 43 is formed having a cutout shape with an opening at the base end portion of the gas sensor 1 in the longitudinal direction L. The reference gas chamber 102 is formed having three sides enclosed by the third insulating plate 43, between the second surface 202 of the solid electrolyte plate 2 and the ceramic substrates 51. The reference gas A flows into the reference gas chamber 102 from the base end portion of the gas sensor 1 in the longitudinal direction L.

As shown in FIG. 4, the conductor layer 52 of the heater 5 includes a pair of lead parts 521 which are connected to an electric conduction means located outside of the gas sensor 1, and a heat-generating portion 522 which connects the pair of lead parts 521 and generates heat when supplied with power by a voltage applied to the pair of lead parts 521. When the conductor layer 52 is supplied with power, the heat-generating portion 522 mainly generates heat by Joule heating. As a result of such heat generation by the heat-generating portion 522, the temperatures of the pump electrode 21, the monitor electrode 22, and the sensor electrode 23 are increased to desired operating temperatures.

The resistance value of the heat-generating portion 522 is greater than the resistance of the lead parts 521. The resistance value of the heat-generating portion 522 can account for at least 50% of the resistance value of the entire conductor layer 52. The heat-generating portion 522 is provided in a position facing substantially an entire planar region in which the pump electrode 21, the monitor electrode 22, and the sensor electrode 23 are disposed.

The resistance value of the heat-generating portion 522 can be set greater than the resistance value of the lead part 521 by making a pattern wiring for the heat-generating portion 522 thinner than a pattern wiring for the lead part 521. Alternatively, by setting the thickness of the heat-generating portion 522 less than the thickness of the lead part 521 or by using a material having a specific resistance higher than the resistivity of a constituent of the lead part 521 as a constituent of the heat-generating portion 522, for example, the resistance value of the heat-generating portion 522 can also be set greater than the resistance value of the lead part 521. Furthermore, the resistance value of the heat-generating portion 522 can also be set greater than the resistance value of the lead part 521 by combining methods of changing the width, thickness, constituent, etc. of the pattern wiring.

As shown in FIG. 1, the pump cell 31 includes the pump electrode 21, a portion of the reference electrode 24, and the first portion 2A of the solid electrolyte plate 2 that is located between the pump electrode 21 and the portion of the reference electrode 24. A voltage application circuit 61 which applies a voltage between these electrodes 21 and 24 is provided between the pump electrode 21 and the reference electrode 24. When the voltage application circuit 61 applies a voltage between the pump electrode 21 and the reference electrode 24, oxygen contained in the measured gas G which contacts the pump electrode 21 is decomposed, and oxygen ions are permeate to the reference electrode 24 through the solid electrolyte plate 2, resulting in removal of the oxygen contained in the measured gas G in the measured gas chamber 101.

As shown in FIG. 2, the monitor cell 32 includes the monitor electrode 22, the portion of the reference electrode 24, and the second portion 2B of the solid electrolyte plate 2 that is located between the monitor electrode 22 and the portion of the reference electrode 24. A monitor current detection circuit 62 which detects an electric current flowing between the monitor electrode 22 and the reference electrode 24 in a state where a predetermined voltage is applied between these electrodes 22 and 24 is provided between these electrodes 22 and 24. When the residual oxygen contained in the measured gas G that contacts the monitor electrode 22 is decomposed, oxygen ions migrate to the reference electrode 24 through the solid electrolyte plate 2. At this time, the monitor current detection circuit 62 detects the electric current flowing between the monitor electrode 22 and the reference electrode 24 through the second portion 2B of the solid electrolyte plate 2.

As shown in this figure, the sensor cell 33 includes the sensor electrode 23, the portion of the reference electrode 24, and the third portion 2C of the solid electrolyte plate 2 that is located between the sensor electrode 23 and the portion of the reference electrode 24. A sensor current detection circuit 63 which detects an electric current flowing between the sensor electrode 23 and the reference electrode 24 in a state where a predetermined voltage is applied between these electrodes 23 and 24 is provided between these electrodes 23 and 24. When the residual oxygen and the specific gas component contained in the measured gas G that contacts the sensor electrode 23 are decomposed, oxygen ions migrate to the reference electrode 24 through the solid electrolyte plate 2. At this time, the sensor current detection circuit 63 detects the electric current flowing between the sensor electrode 23 and the reference electrode 24 through the third portion 2C of the solid electrolyte plate 2.

Furthermore, in a control unit which controls operations of the gas sensor 1, the electric current output of the monitor cell 32 is subtracted from the electric current output of the sensor cell 33, and thus an influence of the residual oxygen contained in the exhaust gas which is the measured gas G is corrected before the concentration of $NO_x$, which is the specific gas component, is determined.

The gas sensor 1 is formed by laminating a zirconia sheet constituting the solid electrolyte plate 2, the respective insulating plates 41, 42, and 43, the diffusion resistor 44, and the heater 5, and sintering this laminated body. At this time, paste of electrode materials that constitute the pump electrode 21, the monitor electrode 22, the sensor electrode 23, and the reference electrode 24 is applied in planar form to a surface of the zirconia sheet. Note that metal components and zirconia components in the electrodes 21, 22, 23, and 24 are not fully diffused in planar form; the sintered electrodes 21, 22, 23, and 24 have microscopically uneven surfaces. Therefore, in order to clarify the thicknesses of the monitor electrode 22 and the sensor electrode 23, the thicknesses of the monitor electrode 22 and the sensor electrode 23 are denoted as maximum thicknesses t1 and t2. The difference between the maximum thickness and the minimum thickness of each of the monitor electrode 22 and the sensor electrode 23 is set equal to or less than 3 μm.

Here, the maximum thicknesses t1 and t2 indicate the thicknesses of the electrodes 22 and 23 having the uneven surfaces, in positions in which the thicknesses are greatest. The surfaces of the electrodes 22 and 23 have many depressed portions formed by pores; the maximum thicknesses t1 and t2 are the thicknesses in the selected area not including the depressed portions. Each of end portions 221 and 231 of the respective electrodes 22 and 23 is often formed into not a right-angle shape, but the shape of a circular arc (indicated by the two-dot chain line) or the like as shown in FIG. 5. Therefore, the maximum thicknesses t1 and t2 are measured as the thicknesses of the electrodes 22 and 23 near central portions thereof other than the entire end portions 221 and 231 in a plan view.

The maximum thicknesses t1 and t2 of the electrodes 22 and 23 can be measured through observation using an optical microscope or an electron microscope. The maximum thicknesses t1 and t2 of the electrodes 22 and 23 can be measured, for example, by cutting the electrodes 22 and 23 by ion beam processing or the like and then observing these cut surfaces by scanning electron microscopy (SEM) or the like.

The maximum thickness t2 of the sensor electrode 23 in the present embodiment is between 5 μm and 35 μm, inclusive, and the maximum thickness t1 of the monitor electrode 22 in the present embodiment is between 3 μm and 20 μm, inclusive. The difference between the maximum thickness t2 of the sensor electrode 23 and the maximum thickness t1 of the monitor electrode 22 can be set in a range between 5 μm and 10 μm, inclusive.

In the present embodiment, an appropriate range of the maximum thickness t1 of the monitor electrode 22, an appropriate range of the maximum thickness t2 of the sensor electrode 23, and an appropriate range of the difference between the maximum thickness t2 of the sensor electrode 23 and the maximum thickness t1 of the monitor electrode 22 are verified. In the following tests in FIGS. 7 to 11, the metal component of each of the pump electrode 21 and the monitor electrode 22 was set to a Pt-Au alloy containing 99% by mass of Pt and 1% by mass of Au, and the metal component of the sensor electrode 23 was set to a Pt-Rh alloy containing 50% by mass of Pt and 50% by mass of Rh.

Figure 7:
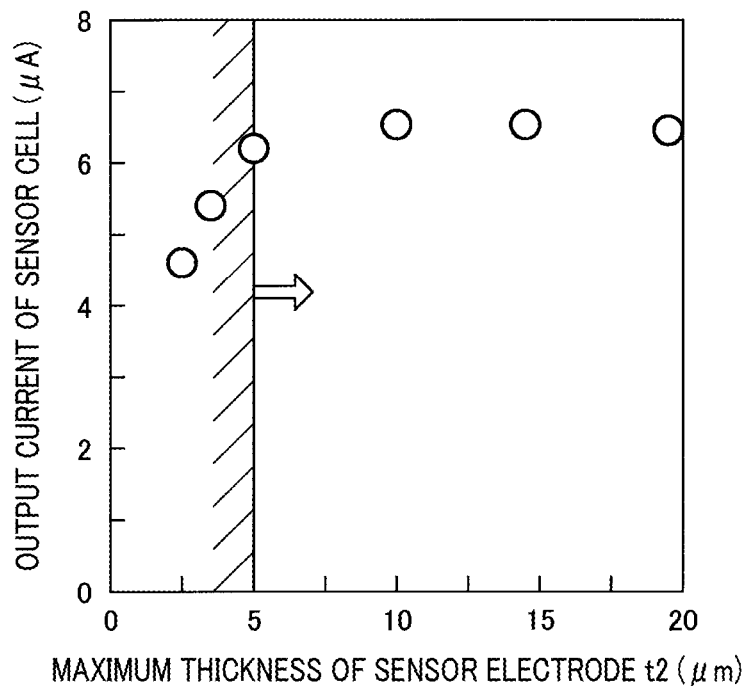
FIG. 7 is a graph showing a relationship between the maximum thickness of the sensor electrode and an output current of a sensor cell according to the embodiment.

FIG. 7 shows results of a test conducted focusing on a relationship between the maximum thickness t2 (μm) of the sensor electrode 23 and the output current (μA) of the sensor cell 33. In this test, a plurality of gas sensors 1 including sensor electrodes 23 having different maximum thicknesses t2 were prepared, and an output current of the sensor cell 33 in each of the gas sensors 1 was measured. A measured gas G having an oxygen concentration of 5% and a nitric oxide (NO) concentration of 2,000 ppm, the rest of which was nitrogen, was introduced into the measured gas chamber 101 of each of the gas sensors 1. The output current of the sensor cell 33 is the output current of the sensor cell 33 in each of the gas sensors 1 measured upon the detection of the concentration of the nitric oxide as the specific gas component. The maximum thickness t1 of the monitor electrode 22 was set to 10 μm.

As shown in the figure that the output current of the sensor cell 33 does not significantly change in a range where the maximum thickness t2 of the sensor electrode 23 is 5 μm or more. This is because the nitric oxide is completely decomposed in this range, and a rate at which the measured gas G is introduced by the diffusion resistor 44 into the measured gas chamber 101 is limited. Furthermore, it can be seen that the output current of the sensor cell 33 decreases as the maximum thickness t2 of the sensor electrode 23 becomes less than 5 μm. The reason for this is considered to be that the surface area of the sensor electrode 23 decreases as a result of a decrease in the maximum thickness t2 of the sensor electrode 23, and insufficiency of reaction points (frequency of contact) between the sensor electrode 23 and the nitric oxide causes a failure of complete decomposition of the nitric oxide introduced into the measured gas chamber 101.

In the sensor cell 33 including the sensor electrode 23, it is necessary to detect a limiting current for complete decomposition of the specific gas component introduced into the measured gas chamber 101. Thus, the maximum thickness t2 of the sensor electrode 23 is preferably 5 μm or more.

Figure 8:
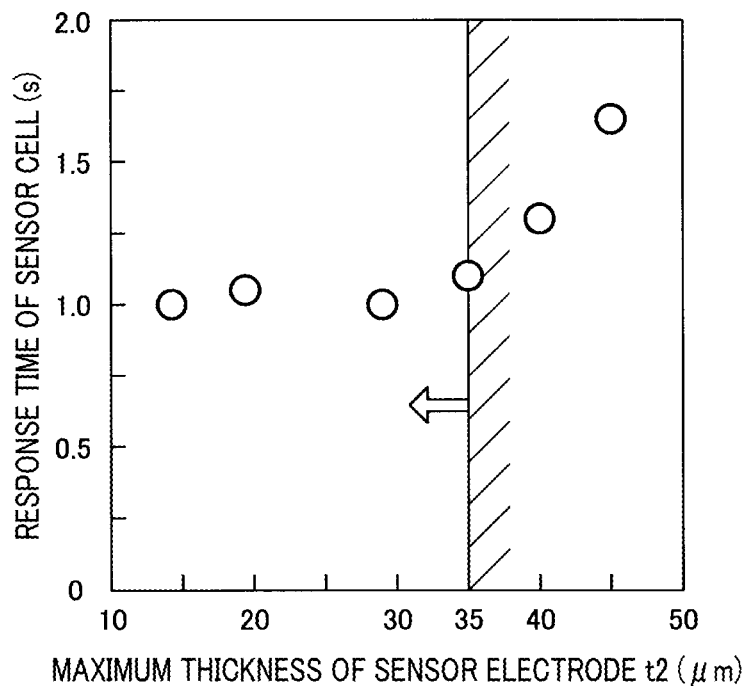
FIG. 8 is a graph showing a relationship between the maximum thickness of the sensor electrode and a response time of the sensor cell according to the embodiment.

FIG. 8 shows results of a test conducted focusing on a relationship between the maximum thickness t2 (μm) of the sensor electrode 23 and the response time (s) of the sensor cell 33. In this test, a plurality of gas sensors 1 including sensor electrodes 23 having different maximum thicknesses t2 were prepared, and the response time of the sensor cell 33 in each of the gas sensors 1 was measured. A measured gas G having an oxygen concentration of 5% and a nitric oxide (NO) concentration of 500 ppm, the rest of which was nitrogen, was introduced first into the measured gas chamber 101 of each of the gas sensors 1. Next, 10-90% response time upon switching of the measured gas G to a measured gas G having an oxygen concentration of 5% and a nitric oxide concentration of 0 ppm, the rest of which was nitrogen, was measured. The maximum thickness t1 of the monitor electrode 22 was set to 10 μm.

As shown in the figure that the response time of the sensor cell 33 does not significantly change in a range where the maximum thickness t2 of the sensor electrode 23 is 35 μm or less. This is because the nitric oxide adsorbed to the sensor electrode 23 is quickly decomposed. Furthermore, it can be seen that the response time of the sensor cell 33 increases as the maximum thickness t2 of the sensor electrode 23 becomes greater than 35 μm. The reason for this is considered to be that an increase in the maximum thickness t2 of the sensor electrode 23 causes an increase in the surface area of the sensor electrode 23, which is a porous body, and thus an increased amount of nitric oxide is adsorbed to the sensor electrode 23, resulting in an increase in time required for the nitric oxide to separate from the sensor electrode 23.

Since the response time of the sensor cell 33 including the sensor electrode 23 needs to be kept short, the maximum thickness t2 of the sensor electrode 23 is preferably 35 μm or less.

Figure 9:
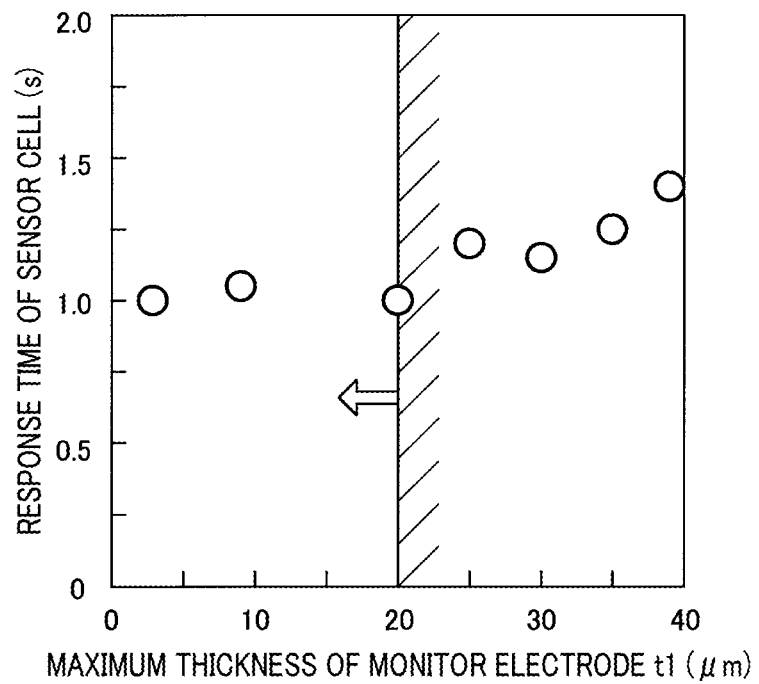
FIG. 9 is a graph showing a relationship between the maximum thickness of the monitor electrode and a response time of the sensor cell according to the embodiment.

FIG. 9 shows results of a test conducted focusing on a relationship between the maximum thickness t1 (μm) of the monitor electrode 22 and the response time (s) of the sensor cell 33. In this test, a plurality of gas sensors 1 including monitor electrodes 22 having different maximum thicknesses t1 were prepared, and the response time of the sensor cell 33 in each of the gas sensors 1 was measured. The measured gas G having an oxygen concentration of 5% and a nitric oxide (NO) concentration of 500 ppm, the rest of which was nitrogen, was introduced first into the measured gas chamber 101 of each of the gas sensors 1. Next, 10-90% response time upon switching of the measured gas G to a measured gas G having an oxygen concentration of 5% and a nitric oxide concentration of 0 ppm, the rest of which was nitrogen, was measured. The maximum thickness t2 of the sensor electrode 23 was set to 10 μm.

As shown in the figure that the response time of the sensor cell 33 does not significantly change in a range where the maximum thickness t1 of the monitor electrode 22 is 20 μm or less. This is because the nitric oxide is less likely to stay on or be adsorbed to the monitor electrode 22 in this range. Furthermore, it can be seen that the response time of the sensor cell 33 increases as the maximum thickness t1 of the monitor electrode 22 becomes greater than 20 μm. The reason for this is considered to be as follows. Specifically, an increase in the maximum thickness t1 of the monitor electrode 22 causes an increase in the surface area of the monitor electrode 22, which is a porous body, and thus an increased amount of nitric oxide is adsorbed to the monitor electrode 22 or stays on a porous part of the monitor electrode 22. Then, the nitric oxide diffused from the monitor electrode 22 reaches the sensor electrode 23, and this nitric oxide is decomposed in the sensor electrode 23.

Since the response time of the sensor cell 33 including the sensor electrode 23 needs to be kept short, the maximum thickness t1 of the monitor electrode 22 is preferably 20 μm or less.

Figure 10:
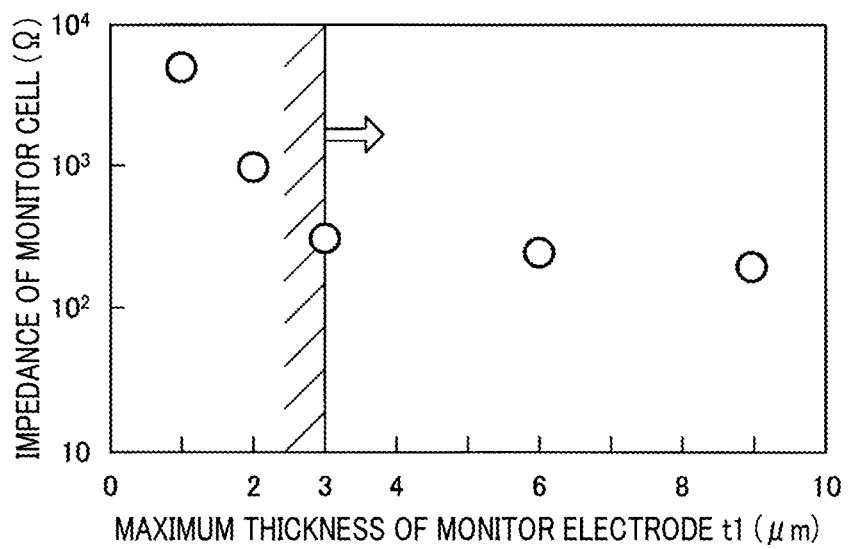
FIG. 10 is a graph showing a relationship between the maximum thickness of the monitor electrode and an impedance of the monitor cell according to the embodiment.

FIG. 10 shows results of a test conducted focusing on a relationship between the maximum thickness t1 (μm) of the monitor electrode 22 and an impedance (Ω) of the monitor cell 32. In this test, a plurality of gas sensors 1 including monitor electrodes 22 having different maximum thicknesses t1 were prepared, and the impedance of the monitor cell 32 in each of the gas sensors 1 was measured. The impedance of the monitor cell 32 is indicated as a value at a frequency of 10 kHz. The impedance of the monitor cell 32 is represented as a sum of the internal resistance of the monitor electrode 22, the internal resistance of the solid electrolyte plate 2, and the interface resistance between the monitor electrode 22 and the solid electrolyte plate 2, for example.

As shown in the figure that the impedance of the monitor cell 32 does not significantly change in a range where the maximum thickness t1 of the monitor electrode 22 is 3 μm or more. Furthermore, it can be seen that the impedance of the monitor cell 32 increases as the maximum thickness t1 of the monitor electrode 22 becomes less than 3 μm. This is because the internal resistance of the monitor electrode 22, etc. increases as a result of a decrease in the maximum thickness t1 of the monitor electrode 22.

When the impedance of the monitor cell 32 is high, the decomposition of the residual oxygen in the monitor cell 32 is delayed, and as a result, the detection accuracy of the monitor cell 32 deteriorates. Thus, the maximum thickness t1 of the monitor electrode 22 is preferably 3 μm or more.

Figure 11:
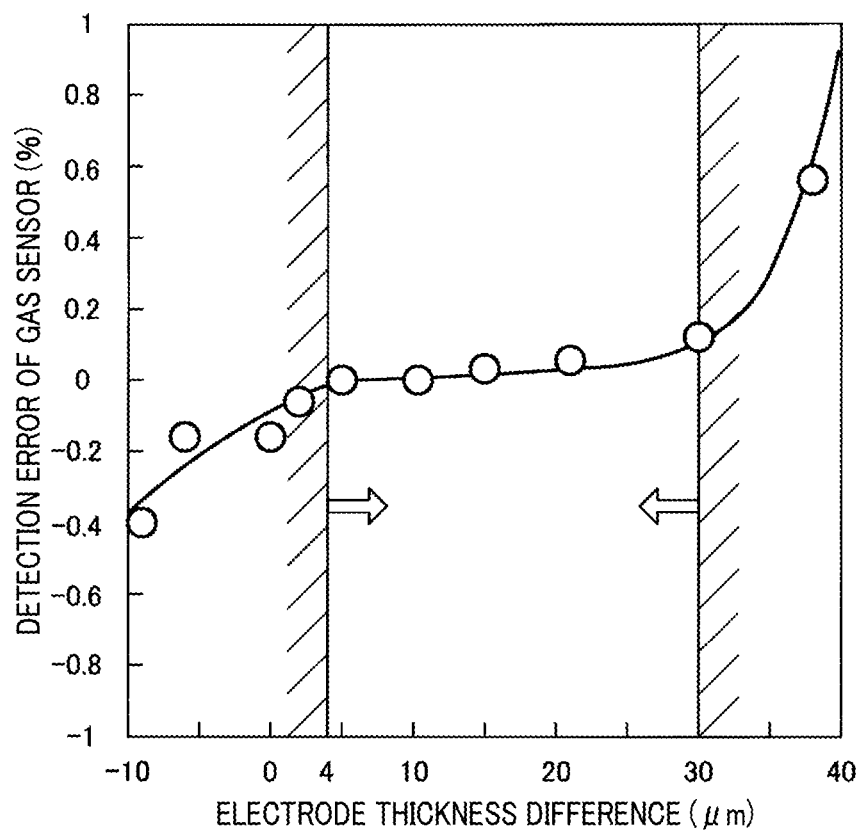
FIG. 11 is a graph showing a relationship between a detection error of the gas sensor and a difference between the maximum thickness of the sensor electrode and the maximum thickness of the monitor electrode according to the embodiment.

FIG. 11 shows results of a test conducted focusing on a relationship between a detection error (%) of the gas sensor 1 and the difference (referred to as an electrode thickness difference) between the maximum thickness t2 of the sensor electrode 23 and the maximum thickness t1 of the monitor electrode 22. In this test, a plurality of gas sensors 1 having different electrode thicknesses were prepared, a measured gas G having an oxygen concentration of 5% and a nitric oxide (NO) concentration of 100 ppm, the rest of which was nitrogen, was introduced into the measured gas chamber 101 of each of the gas sensors 1, and the nitric oxide concentration was detected using each of the gas sensors 1. An error in the nitric oxide concentration detected by the gas sensor 1 relative to the actual nitric oxide concentration (of 100 ppm) is shown as the detection error.

As shown in the figures that there is no large detection error occurring in the gas sensor 1 when the electrode thickness difference is in a range of 4 μm to 30 μm.

Furthermore, it can be seen that a positive detection error increases as the electrode thickness difference becomes greater than 30 μm. The reason for this is considered to be as follows. Specifically, with an increase in the maximum thicknesses t1 and t2 of the electrodes 22 and 23, there are more opportunities of contact between the electrodes 22 and 23 and the residual oxygen (oxygen molecules) in the measured gas chamber 101, and thus the electrodes 22 and 23 have higher sensitivity to the residual oxygen. Then, when the electrode thickness difference becomes greater than 30 μm, the sensitivity of the sensor electrode 23 to the residual oxygen becomes excessively higher than the sensitivity of the monitor electrode 22 to the residual oxygen, leading to a large positive detection error. Here, the positive detection error means an error that the nitric oxide concentration detected by the gas sensor 1 is extremely high relative to the actual nitric oxide concentration.

On the other hand, it can be seen that a negative detection error increases as the electrode thickness difference becomes less than 4 μm. The reason for this is considered to be that because the sensitivity of the sensor electrode 23 to the residual oxygen cannot be sufficient while the sensitivity of the monitor electrode 22 to the residual oxygen is secured to be high enough. Here, the negative detection error means an error that the nitric oxide concentration detected by the gas sensor 1 is extremely low relative to the actual nitric oxide concentration.

Furthermore, according to the above-mentioned results, the difference between the maximum thickness t2 of the sensor electrode 23 and the maximum thickness t1 of the monitor electrode 22 is preferably 4 μm or more. The reason for this is considered to be as follows. Specifically, a component of each of the electrodes 22 and 23 that has high activity against the residual oxygen (oxygen molecules) is Pt.

In the present test, the metal component of the monitor electrode 22 contains 99% by mass of Pt and 1% by mass of Au, and the metal component of the sensor electrode 23 contains 50% by mass of Pt and 50% by mass of Rh. The Pt content in the monitor electrode 22 is higher than the Pt content in the sensor electrode 23. Therefore, it is considered that when the maximum thickness t2 of the sensor electrode 23 is greater than the maximum thickness t1 of the monitor electrode 22, a balance can be made between the sensitivities of the electrodes 22 and 23 to the residual oxygen. Thus, the difference between the maximum thickness t2 of the sensor electrode 23 and the maximum thickness t1 of the monitor electrode 22 is preferably 4 μm or more.

Thus, the maximum thickness t2 of the sensor electrode 23 needs to be set greater than the maximum thickness t1 of the monitor electrode 22 by 4 μm to 30 μm. Furthermore, from the perspective of reducing the detection error, the maximum thickness t2 of the sensor electrode 23 is more preferably set greater than the maximum thickness t1 of the monitor electrode 22 by 5 μm to 10 μm.

As described above, while it is sufficient that the monitor electrode 22 contain Pt which decomposes oxygen, the sensor electrode 23 needs to contain, in addition to Pt which decomposes oxygen, Rh and the like which decompose the specific gas component. Thus, the component of the sensor electrode 23 that decomposes oxygen becomes less than the component of the monitor electrode 22 that decomposes oxygen. As a result, the oxygen decomposition ability of the sensor electrode 23 per unit volume becomes relatively less than the oxygen decomposition ability of the monitor electrode 22 per unit volume. In order to balance between the oxygen decomposition ability of the monitor electrode 22 and the oxygen decomposition ability of the sensor electrode 23, it is effective to set the maximum thickness t2 of the sensor electrode 23 greater than the maximum thickness t1 of the monitor electrode 22. Thus, as a result of setting the maximum thickness t2 of the sensor electrode 23 greater than the maximum thickness t1 of the monitor electrode 22, the accuracy in detecting the specific gas component by the gas sensor 1 can be improved.

When the maximum thickness t1 of the sensor electrode 23 is excessively greater than the maximum thickness t2 of the monitor electrode 22, the sensitivity of the sensor electrode 23 to the specific gas component would become high, while the sensitivity of the sensor electrode 23 to the residual oxygen may become excessively greater than the sensitivity of the monitor electrode 22 to the residual oxygen. Therefore, by setting the difference between the maximum thickness t2 of the sensor electrode 23 and the maximum thickness t1 of the monitor electrode 22 equal to or less than 30 μm, the difference between the sensitivity of the sensor electrode 23 to the residual oxygen and the sensitivity of the monitor electrode 22 to the residual oxygen can be prevented from becoming large. Thus, as a result of properly correcting for the influence that the residual oxygen has on the detection of the specific gas component, the accuracy in detecting the specific gas component by the gas sensor 1 can be improved.

However, in order to balance between the oxygen decomposition ability of the monitor electrode 22 and the oxygen decomposition ability of the sensor electrode 23, the maximum thickness t2 of the sensor electrode 23 needs to be at least 4 μm greater than the maximum thickness t1 of the monitor electrode 22.

Thus, with the above-mentioned gas sensor 1 according to the present embodiment, the accuracy in detecting the specific gas component can be improved by properly correcting for the influence of the residual oxygen.

The structure of the gas sensor 1 is not limited to the structure described above and may have another structure in which the pump cell 31, the monitor cell 32, the sensor cell 33, and the like are formed.

Figure 12:
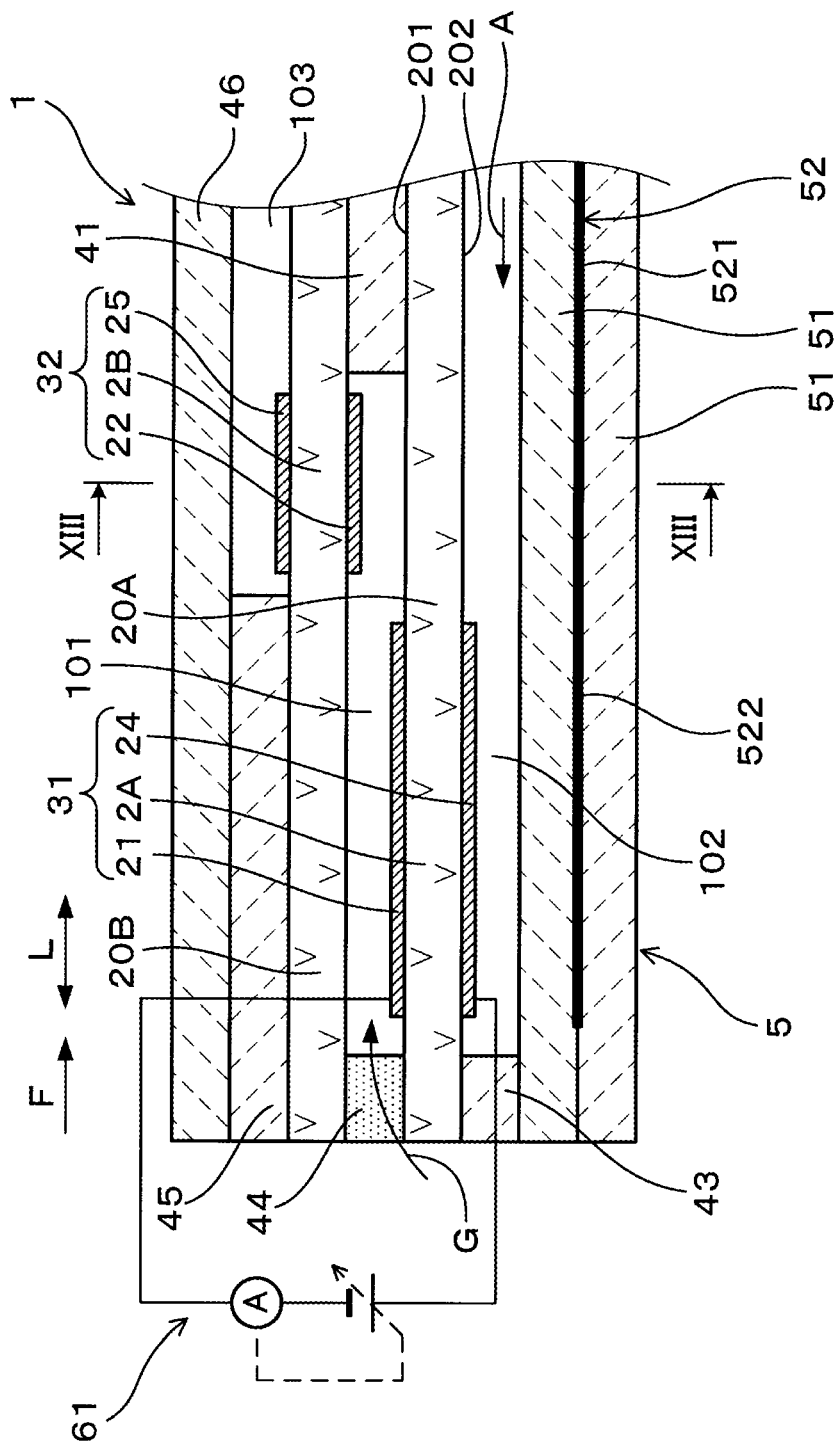
FIG. 12 illustrates a cross sectional view of another gas sensor according to an embodiment.
Figure 13:
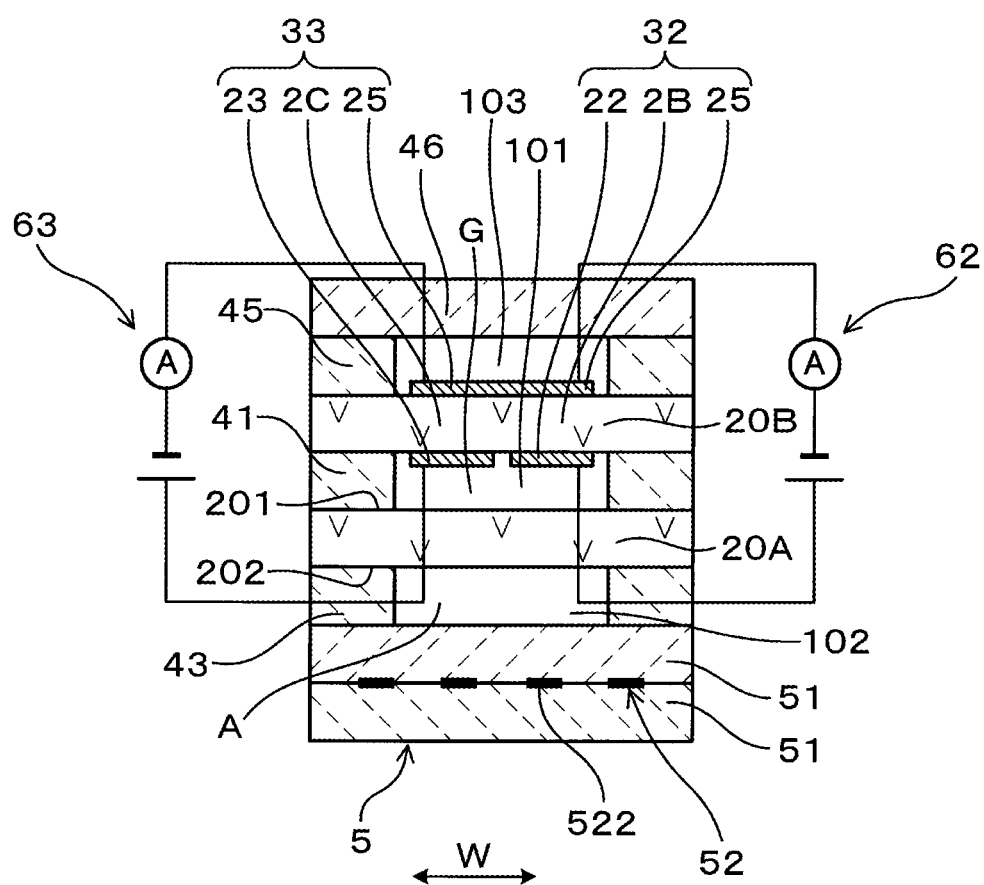
FIG. 13 illustrates a cross sectional view of the gas sensor according to the embodiment, taken in a direction of arrows XIII-XIII in FIG. 12.

For example, as shown in FIGS. 12 and 13, the pump electrode 21 may be provided on a solid electrolyte plate 20A different from a solid electrolyte plate 20B on which the monitor electrode 22 and the sensor electrode 23 are provided. In this case, the gas sensor 1 includes the first solid electrolyte plate 20A on which the pump electrode 21 is provided and the second solid electrolyte plate 20B on which the monitor electrode 22 and the sensor electrode 23 are provided. The second solid electrolyte plate 20B is laminated above the first solid electrolyte plate 20A via the first insulating plate 41 and the diffusion resistor 44, and another reference electrode 25 is provided on a surface of the second solid electrolyte plate 20B opposite to a surface thereof on which the monitor electrode 22 and the sensor electrode 23 are provided. Furthermore, a fourth insulating plate 45 and a fifth insulating plate 46 for forming another reference gas chamber 103 are laminated above the second solid electrolyte plate 20B, and another reference electrode 25 is disposed in another reference gas chamber 103.

In this case, the maximum thickness t1 of the monitor electrode 22 and the maximum thickness t2 of the sensor electrode 23 can also be set as in the above embodiment.

The present disclosure is not limited to only the above embodiment and can be applied to a different embodiment within a scope that does not depart from the essence of the present disclosure.

The invention claimed is:

1. A gas sensor comprising:
one or more solid electrolyte plate having oxygen ion conductivity;
a measured gas chamber formed adjacent to the solid electrolyte plate;
a pump electrode which is provided on a surface of the solid electrolyte plate and is exposed to a measured gas in the measured gas chamber;
a monitor electrode and a sensor electrode which are provided adjacent to each other on the surface of the solid electrolyte plate, in positions downstream of the pump electrode in a flow direction of the measured gas, and are exposed to the measured gas in the measured gas chamber;
one or more reference electrode which is provided on a surface of the solid electrolyte plate and is exposed to a reference gas;
a heater which is disposed facing the solid electrolyte plate and heats the solid electrolyte plate;
a pump cell which adjusts an oxygen concentration of the measured gas in the measured gas chamber when a voltage is applied between the pump electrode and the reference electrode through a first portion of the solid electrolyte plate;
a monitor cell which detects an electric current flowing between the monitor electrode and the reference electrode through a second portion of the solid electrolyte plate, and detects residual oxygen in the measured gas having the oxygen concentration adjusted by the pump electrode; and
a sensor cell which detects an electric current flowing between the sensor electrode and the reference electrode through a third portion of the solid electrolyte plate, and detects the residual oxygen and a specific gas component in the measured gas having the oxygen concentration adjusted by the pump electrode, wherein
a maximum thickness of the sensor electrode is greater than a maximum thickness of the monitor electrode, and a difference between the maximum thickness of the sensor electrode and the maximum thickness of the monitor electrode is between 4 µm and 30 µm, inclusive.

2. A gas sensor comprising:
one or more solid electrolyte plate having oxygen ion conductivity;
a measured gas chamber formed adjacent to the solid electrolyte plate;
a pump electrode which is provided on a surface of the solid electrolyte plate and is exposed to a measured gas in the measured gas chamber;
a monitor electrode and a sensor electrode which are provided adjacent to each other on the surface of the solid electrolyte plate, in positions downstream of the pump electrode in a flow direction of the measured gas, and are exposed to the measured gas in the measured gas chamber;
one or more reference electrode which is provided on a surface of the solid electrolyte plate and is exposed to a reference gas;
a heater which is disposed facing the solid electrolyte plate and heats the solid electrolyte plate;
a pump cell which adjusts an oxygen concentration of the measured gas in the measured gas chamber when a voltage is applied between the pump electrode and the reference electrode through a first portion of the solid electrolyte plate;
a monitor cell which detects an electric current flowing between the monitor electrode and the reference electrode through a second portion of the solid electrolyte plate, and detects residual oxygen in the measured gas having the oxygen concentration adjusted by the pump electrode; and
a sensor cell which detects an electric current flowing between the sensor electrode and the reference electrode through a third portion of the solid electrolyte plate, and detects the residual oxygen and a specific gas component in the measured gas having the oxygen concentration adjusted by the pump electrode, wherein
the monitor electrode and the sensor electrode are arranged in the same space of the measured gas chamber, and
a maximum thickness of the sensor electrode is greater than a maximum thickness of the monitor electrode, and a difference between the maximum thickness of the sensor electrode and the maximum thickness of the monitor electrode is between 4 µm and 30 µm, inclusive.

3. A gas sensor comprising:
one or more solid electrolyte plate having oxygen ion conductivity;
a measured gas chamber formed adjacent to the solid electrolyte plate;
a pump electrode which is provided on a surface of the solid electrolyte plate and is exposed to a measured gas in the measured gas chamber;
a monitor electrode and a sensor electrode which are provided adjacent to each other on the surface of the solid electrolyte plate, in positions downstream of the pump electrode in a flow direction of the measured gas, and are exposed to the measured gas in the measured gas chamber;

one or more reference electrode which is provided on a surface of the solid electrolyte plate and is exposed to a reference gas;

a heater which is disposed facing the solid electrolyte plate and heats the solid electrolyte plate;

a pump cell which adjusts an oxygen concentration of the measured gas in the measured gas chamber when a voltage is applied between the pump electrode and the reference electrode through a first portion of the solid electrolyte plate;

a monitor cell which detects an electric current flowing between the monitor electrode and the reference electrode through a second portion of the solid electrolyte plate, and detects residual oxygen in the measured gas having the oxygen concentration adjusted by the pump electrode; and a sensor cell which detects an electric current flowing between the sensor electrode and the reference electrode through a third portion of the solid electrolyte plate, and detects the residual oxygen and a specific gas component in the measured gas having the oxygen concentration adjusted by the pump electrode, wherein the entire monitor electrode is composed of a cermet material containing a metal component capable of decomposing oxygen and not decomposing a specific gas component, the entire sensor electrode is composed of a cermet material containing a metal component capable of decomposing oxygen and the specific gas component, and a maximum thickness of the sensor electrode is greater than a maximum thickness of the monitor electrode, and a difference between the maximum thickness of the sensor electrode and the maximum thickness of the monitor electrode is between 4 μm and 30 μm, inclusive.

4. The gas sensor according to claim 1 wherein
the monitor electrode and the sensor electrode are arranged side by side in a direction perpendicular to a flow direction of the measured gas downstream of an arrangement position of the pump electrode in the measured gas chamber.

5. The gas sensor according to claim 2 wherein
the monitor electrode and the sensor electrode are arranged side by side in a direction perpendicular to a flow direction of the measured gas downstream of an arrangement position of the pump electrode in the measured gas chamber.

6. The gas sensor according to claim 3 wherein
the monitor electrode and the sensor electrode are arranged side by side in a direction perpendicular to a flow direction of the measured gas downstream of an arrangement position of the pump electrode in the measured gas chamber.

7. The gas sensor according to claim 1 wherein
the difference between the maximum thickness of the sensor electrode and the maximum thickness of the monitor electrode is between 5 μm and 10 μm, inclusive.

8. The gas sensor according to claim 2 wherein
the difference between the maximum thickness of the sensor electrode and the maximum thickness of the monitor electrode is between 5 μm and 10 μm, inclusive.

9. The gas sensor according to claim 3 wherein
the difference between the maximum thickness of the sensor electrode and the maximum thickness of the monitor electrode is between 5 μm and 10 μm, inclusive.

10. The gas sensor according to claim 1 wherein
the maximum thickness of the sensor electrode is between 5 μm and 35 μm, inclusive.

11. The gas sensor according to claim 2 wherein
the maximum thickness of the sensor electrode is between 5 μm and 35 μm, inclusive.

12. The gas sensor according to claim 3 wherein
the maximum thickness of the sensor electrode is between 5 μm and 35 μm, inclusive.

13. The gas sensor according to claim 1 wherein
the maximum thickness of the monitor electrode is between 3 μm and 20 μm, inclusive.

14. The gas sensor according to claim 2 wherein
the maximum thickness of the monitor electrode is between 3 μm and 20 μm, inclusive.

15. The gas sensor according to claim 3 wherein
the maximum thickness of the monitor electrode is between 3 μm and 20 μm, inclusive.

* * * * *